US006352726B1

(12) United States Patent
Haas et al.

(10) Patent No.: US 6,352,726 B1
(45) Date of Patent: Mar. 5, 2002

(54) METHOD OF KILLING PROTOZOA

(75) Inventors: Gerhard J. Haas, Woodcliff Lake; Vanita Srinivasan, Avenel, both of NJ (US)

(73) Assignee: S. S. Steiner, Inc., New York, NY (US)

( * ) Notice: Subject to any disclaimer, the term of this patent is extended or adjusted under 35 U.S.C. 154(b) by 0 days.

(21) Appl. No.: 09/756,629

(22) Filed: Jan. 9, 2001

(51) Int. Cl.⁷ ............................................... A61K 35/78
(52) U.S. Cl. ....................... 424/725; 424/776; 426/600; 514/690; 568/366
(58) Field of Search ................. 424/725, 776; 514/690; 568/366; 426/600

(56) References Cited

U.S. PATENT DOCUMENTS 4,590,296 A  * 5/1986 Cowles et al. .............. 568/366
5,827,895 A  * 10/1998 Nutter et al. ................ 514/690

OTHER PUBLICATIONS

Greenwald et al. PDR for Herbal Medicines, 1998. Medical Economic Company, Inc., Montvale, N.J., pp. 900–901.*

Budavari et al. The Merck Index, 1989. Merck & Co., Inc., Rahway, N.J., p. 882.*

* cited by examiner

Primary Examiner—Christopher R. Tate
Assistant Examiner—Kailash C. Srivastava
(74) Attorney, Agent, or Firm—Walter D. Ames, Esq.

(57) ABSTRACT

A method of killing protozoa comprises subjecting the protozoa to an effective amount of extract of the hop plant. Such protozoicidal effect is increased when the hop extract is further treated with carbon dioxide.

7 Claims, No Drawings

METHOD OF KILLING PROTOZOA

FIELD OF THE INVENTION

The present invention relates generally to processes having an antimicrobial objective. More specifically, it relates to protozoicides, that is, processes for the killing of protozoa.

BACKGROUND OF THE INVENTION

The hop plant, Humulus lupulus, is a twining vine that is a member of the mulberry (Cannabinaceae) family. It has inconspicuous flowers, the pistillate ones of which form glandular, cone-shaped catkins which, when ripe and dried, find familiar use to impart a bitter flavor to beverages derived from malt. Hop has been used to flavor and preserve wort and beer since the 12th century in Germany and the 15th century in England. Its resins, which reside in the yellow glands of its cones, have been known to possess antimicrobial properties. Those resins are extracted from the cones, usually by supercritical carbon dioxide treatment, or by extraction with organic solvents, and are today most often used in the form of extracts.

With respect to the chemical nature of hop compounds, they are weak acids classified as alpha bitter resins and beta bitter resins or bitter acids. Alpha bitter acids are represented by humulone and its cogeners, cohumulone, adhumulone, prehumulone and posthumulone. The beta resins are represented by lupulone, and its cogeners, colupulone, adlupulone, and prelupulone. The alpha and beta acids have alicyclic structures (2,4-cyclohexodine-1-one), but their cogeners differ in the nature of the acyl side chain. While the alpha acids and their derivatives, the iso acids, contribute most to the bitterness of beer, there are many other, sometimes minor constituents that contribute to preservation and bitterness. One of these compounds is xanthohumol, which has also been found to fall within the scope of the present invention.

The antimicrobial properties of hop compounds are well-known; their extracts primarily are used to inhibit the growth of gram positive microbes, and they are usually inactive against gram negative bacteria. Yeast is not inhibited by hop compounds. Fungi are either not inhibited or inhibited at unfavorably high concentrations of hop extracts. Prior to our work, little if anything was known about the effect of hop extracts on protozoa, the only possible exception being work in U.S. Pat. No. 5,827,895 by Nutter et al. about the inhibition of the pathogenic protozoa Leishmania by a chemically modified hop derivative, hexahydrolupulone. However, it has now been found that different hop extracts have a decidedly positive effect in killing a broad range of protozoa.

There are many pathogenic protozoa that lead to human diseases. Among these are *Entameba histolytica, Cryptosporidium parvum, Giardia lamblia*, and others that are pathogenic in the intestinal tract. Campers often have to purify water and remove pathogenic protozoa to make it potable. Still other protozoa are systemic, such as plasmodium, the causative agent of malaria, and trypanosomes.

It is, therefore, a primary object of the present invention to formulate a-process or method for killing protozoa by the use of compositions that are harmless to humans. As will be apparent, the objective of this work has been to achieve that goal.

SUMMARY OF THE INVENTION

The present invention is in the form of a method for killing protozoa. The agent for accomplishing this purpose is an effective amount of extract from the hop plant, which extract is composed of alpha resins, beta resins, xanthohumol and combinations thereof.

When used herein, the term, alpha-resins, is intended to include alpha resins per se, e.g., humulone, and also its derivatives, such as iso alpha resin and tetra iso alpha resin. When alpha resin as so defined is the agent for killing protozoa, it is preferably in the form of the tetra iso alpha resin, which is water-soluble. In this instance the minimum effective amounts of the alpha resin are about 0.2 to about 20 ug/ml. when the protozoa are ciliates or flagellates. When the protozoa are in the form of amoebae, the-minimum effective amount varies from about 100 to about 500 ug/ml., as amoebae appear more resistant to alpha resin than ciliates or flagellates.

When beta resins are utilized with ciliates or flagellates, the effective amount is about 0.1 to about 2.0 ug/ml. Xanthohumol appears to be more lethal to such protozoa than beta resin, the quantity necessary to achieve a 100% kill rate varies from about 0.05 to 1.0 ug/ml.

It has also been discovered that a greatly improved, synergistic effect is obtained when carbon dioxide is used in combination with hop resins against protozoa. Thus, when the extract solution of hop resins is subjected to treatment with carbon dioxide, such as by bubbling carbon dioxide gas through the extract solution prior to subjecting the protozoa to treatment with the solution, a superior kill of protozoa is obtained. For example, when the alpha resin as herein defined is used against ciliates and flagellates, prior treatment of the extract solution with carbon dioxide results in killing the protozoa at a concentration of only 0.05 to 0.1 ug of extract per ml. of solution. The same is true for solutions of beta resins. Amoebae are killed with a concentration of 10 to 100 ug/ml. of hop resin in a solution that has been pre-treated with carbon dioxide.

In still another aspect of the present invention, it has also been discovered that solutions which have been carbonated but without hop extract have a lethal effect on protozoa. Thus, as set forth in the detailed description of one preferred embodiment of our invention, when carbon dioxide was bubbled through an aqueous medium for 30 seconds prior to inoculation of the protozoa without the addition of hop extract, death occurred within about 40 to 50 minutes.

These and other features and advantages of the present invention will be more apparent when considered in connection with the following, detailed description of certain preferred embodiments of our invention.

DETAILED DESCRIPTION OF PREFERRED EMBODIMENTS

The hop resins used in this work were obtained from S. S. Steiner, Inc. of New York, N.Y. Those resins were the alpha resin in the form of a 30% aqueous solution of its iso alpha resin derivative, and tetra iso alpha resin derivative in a 19% aqueous solution. Beta resin, i.e., lupulone, was obtained in pure form, as was xanthohumol (99.3% pure).

With regard to the protozoa used in our tests, in Table 1 the protozoa are listed, as well as the medium from which they were obtained, the temperature and period of incubation. As stated in Table 1, all of the protozoa were obtained from Carolina Biological Supply Co., of Burlington, N.C. Six different protozoa are listed in Table 1. They were used in the examples of protozoicidal activity which follow.

TABLE 1

List of Microorganisms and Materials Used.

| Organism | Medium | Incubation temperature | Incubation Period | Supplier |
|---|---|---|---|---|
| PROTOZOA | | | | |
| Paramecium caudatum | Cerophyll | Room Temp | 24 Hours | All from Carolina Biological Supply Company (Burlington NC) |
| Euglena sp. | Euglena medium | Room Temp | 24 Hours | |
| Tetrahymena pyriformis | Tetrahymena medium | Room Temp | 24 Hours | |
| Polytomella papillata | Polytomella medium | Room Temp | 24 Hours | |
| Amoeba proteus | Wheat medium | Room Temp | 24 Hours | |
| Chaos sp. | Wheat medium | Room Temp | 24 Hours | |

*Room temperature fluctuated between 24° C. and 26° C.

EXAMPLE I

The protozoicidal effect of various hop compounds was determined by preparing different concentrations of hop solution in 10 ml. of medium. The solution was poured into 6×4 multiwell dishes—3424 Mark 2 (Coster, Cambridge, Mass.). An average of 10 microorganisms was added to each well and observed under the stereomicroscope. Results were expressed as the time in minutes for a 100% kill, which was presumed when all of the protozoa had stopped moving. The observation time was 24 hours.

In order to determine whether the protozoa had been killed rather than only temporarily inactivated, the organisms in hop solution were centrifuged, the supernatant removed, and the protozoa placed into fresh medium in which hop was not present. When there was no revival of the organisms, it was concluded that they were dead rather than only temporarily inactivated.

TABLE 2

Protozoicidal effect of Beta Resin
Time of death (in minutes) vs concentration
Observation time 24 hours

| | Concentration of Beta Resin in µg/ml. | | | | | |
|---|---|---|---|---|---|---|
| Organisms | 0.05 | 0.1 | 0.2 | 0.5 | 1.0 | 2.0 |
| P. caudatum | NS | 60 | 5 | 3.5 | 3.0 | 2.0 |
| Euglena sp. | NS | NS | NS | 2.5 | 1.5 | 1.2 |
| T. pyriformis | NS | NS | 15 | 3 | 1.5 | 1.0 |
| P. papillata | NS | NS | 40 | 5 | 3.5 | 2.0 |

*Not Sensitive

In this Example I, the protozoicidal effect of beta resin was measured and tabulated in Table 2. Those results show that at a concentration of 0.05 ug/ml. of beta resin, all of the four protozoa tested, which were ciliates or flagellates, were not sensitive, i.e., they were not killed by the beta resin at that concentration. At a concentration of 0.1 ug/ml., only P. caudatum was killed, and the time for death to occur was one hour. However, at a concentration of 0.2 ug/ml. P. caudatum protozoa died within 5 minutes, while death of T. pyriformis occurred within 15 minutes and P. papillata died within 40 minutes.

At a concentration of 0.5 ug/ml. of beta resin, those three protozoa plus the fourth one tested, Euglena sp., died within five minutes. The time for death to occur diminished for all four protozoa as the concentration of beta resin in solution was increased, until at a concentration of 2.0 ug/ml. death occurred within two minutes for the four test species.

EXAMPLE II

Tests similar to those of Example I were carried out, substituting tetra iso alpha resin for the beta resin of Example I. The results of this Example II are tabulated in Table 3. From this Table it will be seen that tetra iso alpha resin generally was not quite as effective as beta resin, although it was certainly significant in its effect.

TABLE 3

Protozoicidal effect of Tetra Iso Alpha Resin
Time of death (in minutes) vs concentration
Observation time 24 hours

| | Concentration of Tetra Iso Alpha Resin in µg/ml | | | | | | | |
|---|---|---|---|---|---|---|---|---|
| Organisms | 0.1 | 0.2 | 0.5 | 1.0 | 2.0 | 5.0 | 10.0 | 20.0 |
| P. caudatum | NS | 4.0 | 3.5 | 2.5 | 2.0 | ND# | ND | ND |
| Euglena sp. | NS | NS | NS | NS | NS | 10.0 | 3.0 | ND |
| T. pyriformis | NS | 60 | 5.5 | 4 | 2.5 | ND | ND | ND |
| P. papillata | NS | NS | NS | NS | NS | NS | NS | 17.5 |

*Not Sensitive
Not Done

EXAMPLE III

Tests similar to those of Example I were performed using xanthohumol as the hop ingredient. The results of these tests, which were limited to P. caudatum and Chaos sp., are identified in Table 6.

TABLE 6

Protozoicidal effect of Xanthohumol
Time of death (in minutes) vs concentration
Observation time 24 hours

| | Concentration of Xanthohumol in µg/ml. | | | | | |
|---|---|---|---|---|---|---|
| Organisms | 0.01 | 0.05 | 0.1 | 1.0 | 2.0 | 5.0 | 100 |
| P. caudatum | NS* | 10 | 5 | 2.5 | ND** | ND | ND |
| Chaos sp. | NS | NS | NS | NS | NS | 15 | 11 |

*Not Sensitive
**Not Done

Against P. caudatum, xanthohumol was more effective than either the alpha or beta resins of hop. It killed protozoa within ten minutes at a concentration of 0.05 ug/ml., whereas at this concentration neither the alpha nor beta hop compounds were protozoicidal. It was also effective in killing Chaos sp. at concentrations of 5 ug/ml. and greater.

EXAMPLE IV

Tests were conducted to determine the effectiveness of the alpha and beta resins against amoebae. With respect to the tetra iso alpha resin, the results are shown in Table 4. It was only at a concentration of 100 ug/ml. that this resin killed *Chaos sp.*, and it required a concentration of 500 ug/ml. for it to be effective against Amoeba proteus.

TABLE 4

Protozoicidal effect of Tetra Iso Alpha Resin
Time of death (in minutes) vs concentration
Observation time 24 hours

| | Conc. tetra iso alpha in $\mu$g/ml | | | |
|---|---|---|---|---|
| Organisms | 50.0 | 100 | 200 | 500 |
| Amoeba proteus | NS* | NS | NS | 180 |
| Chaos sp. | NS | 240 | 180 | 30 |

*Not Sensitive

EXAMPLE V

The same tests of Example IV were run using the beta hop resin, with the results being tabulated in Table 5. The beta resin was more effective than the tetra iso alpha resin with respect to *Chaos sp.*, and had the same killing ability as the tetra iso alpha resin with respect to Amoeba proteus.

TABLE 5

Protozoicidal effect of Beta Resin
Time of death (in minutes) vs concentration
Observation time 24 hours

| | Conc. Beta Resin in $\mu$g/ml | | | | |
|---|---|---|---|---|---|
| Organisms | 10 | 50 | 100 | 200 | 500 |
| Amoeba proteus | NS* | NS | NS | NS | 180 |
| Chaos sp. | NS | 60 | 30 | 30 | 25 |

*Not Sensitive

It has also been discovered that the protozoicidal ability of the various hop resins is unexpectedly enhanced by the addition of carbon dioxide to the resin solution. Indeed, in some instances in which the resin in a given concentration was not active per se, it was a potent factor at that same concentration when utilized in combination with carbon dioxide. The following two examples illustrate the synergistic effect of hop resin and carbon dioxide on protozoa.

Different concentrations of the alpha and beta resins of hop were prepared in 10 ml. of medium, as identified in Table 1, and poured into plastic tissue culture flasks of 25 cm. growth area with screw caps, obtained from Falcon, Oxnard, Calif. Carbon dioxide was then bubbled through the medium in the bottles at a rapid rate for a period of 30 seconds. An average of ten organisms were added to each flask and examined directly under the stereomicroscope. The times that were taken for a 100% kill of the organisms, that is, when all of the organisms ceased any motion, were recorded in minutes and are tabulated in Tables 7 and 8.

EXAMPLE VI

Table 7 notes the co-action with carbon dioxide of alpha and beta hop resins on *P. caudatum* at two different concentrations: 0.05 and 0.1 ug/ml. All aqueous solutions had previously been subjected to 30 seconds of carbon dioxide treatment by bubbling the gas through the solution. At a concentration of 0.05 ug/ml., neither the alpha nor beta resins were successful alone in causing the death of the protozoa. However, having been preceded by carbon dioxide injection, the beta resin was protozoicidal after 14 minutes and the tetra alpha resin after 18 minutes. At a concentration of 0.1 ug/ml. the beta resin alone had some effect, whereas the alpha resin did not. With prior carbon dioxide treatment both resins were effective after just 5 and 14 minutes, respectively.

TABLE 7

Co-Action of hop resins with Carbon dioxide* on *P. caudatum*
Time of death (in minutes) vs concentration
Observation time 24 hours

| Conc. in $\mu$g/ml | Beta-resin alone | Tetra iso alpha resin alone | Beta resin + $CO_2$ | Tetra iso alpha resin + $CO_2$ |
|---|---|---|---|---|
| 0.05 | NS** | NS | 14 | 18 |
| 0.1 | 60 | NS | 5 | 14 |

*Carbon dioxide had been bubbled into the medium for 30 seconds previous to inoculation and death without addition of hop occured between 40–50 minutes.
**Not Sensitive

EXAMPLE VII

The same tests but at greater resin concentrations were carried out on an amoeba strain, *Chaos sp.*, and the results recorded in Table 8.

TABLE 8

Co-Action of hop resins with Carbon dioxide* on Chaos sp.
Time of death (in minutes) vs concentration
Observation time 24 hours

| Conc. in $\mu$g/ml | Beta-resin alone | Tetra iso alpha resin alone | Beta resin + $CO_2$ | Tetra iso alpha resin + $CO_2$ |
|---|---|---|---|---|
| 10 | NS** | NS | 9 | 16 |
| 50 | 60 | N/S | 6 | 12 |
| 100 | ND*** | 240 | ND | 10 |

*Carbon dioxide had been bubbled into the medium for 30 seconds previous to inoculation and death without addition of hop occurred between 40–50 min.
**Not Sensitive
***Not Done At a concentration of 10 ug/ml. neither the alpha nor beta resins were effective alone. However, with prior carbon dioxide treatment, both were effective, with the pretreated beta resin being more protozoicidal. At a concentration of 50 ug/ml. the beta resin was effective per se, whereas the alpha resin was not. Again, both were effective with carbon dioxide pretreatment. Finally, at a concentration of 100 ug/ml. all were effective, even the alpha resin without pretreatment, and all were most effective with pretreatment.

The conclusions that have been drawn from these tests is that both the alpha and beta resins of hops, as well as the resin xanthohumol, have a definite ability to kill protozoa, with xanthohumol apparently being the most effective and the alpha resin the least, at least at any specific concentration. When subjected to carbon dioxide pretreatment, the killing ability of the hop resins is dramatically enhanced.

Moreover, it has also been found that carbon dioxide impregnated medium, e.g., carbonated water, has a decidedly inhibitory, even killing effect on protozoa. As set forth in the footnotes to Tables 7 and 8 carbon dioxide solutions, when carbon dioxide was bubbled into the medium for 30 seconds prior to inoculation of the protozoa, but without the addition of hop extract, death occurred within 40 to 50 minutes. Thus, carbon dioxide solutions kill both *P. caudatum*-type and *Chaos sp.*-type protozoa. Of course, a source of the carbon dioxide may be other than the pure, gaseous form; for example, it may be generated in situ by the reaction of a carbonate and an acid.

From the above specific examples, it will be apparent to those of skill in the art that certain alterations and modifications may be made to the examples and to the specific hop resins and carbon dioxide pretreatments described without departing from the spirit of the present invention. As to all such alterations and modifications, it is desired that they be included within the purview of this invention, which is to be limited only by the scope, including equivalents, of the following, appended claims.

What is claimed is:

1. A method of killing protozoa, which comprises forming a solution of an effective amount of extract of the hop plant, subjecting said extract solution to carbon dioxide for a period of time sufficient to substantially increase the protozoicidal effect thereof and form a carbonated extract solution, and thereafter subjecting the protozoa to said effective amount of said carbonated extract solution.

2. A method as claimed in claim 1, in which said carbon dioxide is bubbled through said extract solution.

3. A method as claimed in claim 1, in which said carbon dioxide is generated in situ in said extract solution.

4. A method as claimed in claim 1, in which said extract is selected from the group consisting of alpha and beta resins and xanthohumol and combinations thereof, and said protozoa is selected from the group consisting of ciliates and flagellates.

5. A method as claimed in claim 4, in which said effective amount of said carbonated extract solution varies from a minimum of about 0.05 to about 0.1 ug/ml. of hop extract.

6. A method as claimed in claim 4, in which said extract is a beta resin and said protozoa are flagellates.

7. A method as claimed in claim 1, in which said protozoa are amoebae and said effective amount of said carbonated extract solution varies from a minimum of about 10 to about 100 ug/ml. of hop extract.

\* \* \* \* \*